US00PP26347P3

(12) United States Plant Patent
Giumarra et al.

(10) Patent No.: US PP26,347 P3
(45) Date of Patent: Jan. 26, 2016

(54) GRAPE PLANT NAMED 'ARRATWENTYEIGHT'

(50) Latin Name: *Vitis vinifera*
Varietal Denomination: ARRATWENTYEIGHT

(71) Applicant: AGRICULTURAL RESEARCH AND DEVELOPMENT LIMITED LIABILITY COMPANY, Bakersfield, CA (US)

(72) Inventors: Sal Giumarra, Bakersfield, CA (US); Shachar Karniel, Bakersfield, CA (US)

(73) Assignee: Agricultural Research and Development Limited Liability Company, Bakersfield, CA (US)

( * ) Notice: Subject to any disclaimer, the term of this patent is extended or adjusted under 35 U.S.C. 154(b) by 124 days.

(21) Appl. No.: 13/999,815

(22) Filed: Mar. 24, 2014

(65) Prior Publication Data

US 2015/0181785 P1 Jun. 25, 2015

(30) Foreign Application Priority Data

Dec. 23, 2013 (QZ) ..... PBR A201302408

(51) Int. Cl.
*A01H 5/00* (2006.01)

(52) U.S. Cl.
USPC ..... Plt./205

(58) Field of Classification Search
USPC ..... Plt./205
See application file for complete search history.

*Primary Examiner* — Annette Para
(74) *Attorney, Agent, or Firm* — Christie, Parker & Hale, LLP

(57) ABSTRACT

A new distinct variety of grapevine named 'ARRATWENTYEIGHT' abundantly forms attractive large firm and meaty seedless berries with a red skin coloration; in medium-to-large clusters which display natural flavor. The fruit commonly is ready for harvesting during October in San Joaquin Valley of Central California, U.S.A., and displays good eating qualities as a table grape. The fruit firmness renders the fruit well amenable for handling, shipping, and storage.

1 Drawing Sheet

Classification: The present invention relates to a new *Vitis vinifera* Grapevine.

Variety denomination: The new Grapevine has the varietal denomination 'ARRATWENTYEIGHT'.

BACKGROUND OF THE INVENTION

A breeding program was initiated during the late 90's near Bakersfield in San Joaquin Valley of Central California. In 2008, during this breeding program, a new variety of *Vitis vinifera* was created by deliberate cross breeding of two parent plants by emasculation of the pollen bearing organ of the female and introducing pollen from another male origin. The female parent of the new variety was A.3. which is a medium-sized red seedless grape variety with a fleshy texture and a natural flavor (non-patented in the United States). The male parent (i.e. the pollen parent) of the new variety was E.Z. which is a cylinder shaped, white creamy colored, seedless variety with an exotic flavor (non-patented in the United States).

Comparison of 'ARRATWENTYEIGHT' with its parents:

Table 1

| | ARRATWENTYEIGHT | A.3 (Mother) | E.Z. (Father) | Crimson Seedless Comparison Variety |
|---|---|---|---|---|
| Seed Trace | None | Large | None | None |
| Berry shape | Obtuse ovoid | Ovoid | Cylinder | Oblong |
| Bunches per vine | 32 | 48 | 32-36 | 18 |
| Bunch Density | Lax | Medium | Medium-loose | Tight |

The parentage of the new variety can be summarized as follows:

A.3.xE.Z.

An artificial pollination was created, and the result was an embryo which possessed unique genetic qualities. The rudiments resulting from the above pollination were embryo rescued.

In 2009 the plant was transplanted to Bakersfield in San Joaquin Valley of Central California.

It was found that the new grapevine of the present invention possesses the following combination of characteristics:

(a) Forms attractive medium firm & meaty seedless berries with a red skin coloration; in medium-to-large clusters which display a natural flavor, (b) Commonly bears fruit during the month of October in the San Joaquin Valley of Central California, U.S.A., and (c) Bears fruit that is firm and is well amenable for storage, handling, and shipping.

The new variety during observation to date has displayed no visible disease, and has displayed an ability to well resist cold, drought, heat; but sensitive to direct exposure to sun and wind. The fruit of the new variety has been found to display excellent handling and shipping qualities combined with desirable dessert eating qualities.

The new variety of the present invention has been found to undergo asexual propagation beginning in 2010 near Bakersfield in the San Joaquin Valley of Central California, U.S.A. by grafting on mature Thompson rootstock (non-patented in the United States). Such asexual propagation has been conducted thereafter in successive years through 2011, and has shown that the characteristics of the new variety are strictly transmissible from one generation to another. Accordingly, the new variety undergoes asexual propagation in a true to type manner.

SUMMARY OF THE INVENTION

The new variety 'ARRATWENTYEIGHT' is a medium size, red seedless table grape with a medium production, e.g., about 32 bunches per vine, and an average of about one to two bunches per shoot.

Asexual reproduction by micro propagation of the new variety as performed near Bakersfield, Calif., U.S.A., shows that the forgoing and other distinguishing characteristics come true to form and are established and transmitted through succeeding propagations.

BRIEF DESCRIPTION OF THE DRAWING

The accompanying photographic illustration shows typical specimens of vegetative growth of six year old specimens of the new variety, in color as nearly true as it is reasonably possible to make in a color illustration of this character. Colors in the photograph may differ from the color values cited in the detailed botanical description below, which accurately describes the colors of the new Grapevine.

FIG. 1 shows leaves, stems and grapes of 'ARRATWENTYEIGHT'.

DETAILED BOTANICAL DESCRIPTION

The chart used in the identification of colors is The R.H.S. Colour Chart of The ROYAL HORTICULTURAL SOCIETY 1995 edition. The description is based on the observation of plants growing on 'Thompson Seedless' rootstock outdoors near San Joaquin Valley of Central California, U.S.A.

Vine:
- *Vigor.*—Vigorous upright shoots.
- *Productive capacity.*—Bearing at a natural, average capacity. Spur pruning.
- *Trunk.*—Strong and developed. Ranges from 2"-2⅜". Rough with a fibrous, shaggy exterior. Light maple brown coloring.

Time of bud burst: Mar. 13, 2013 in Bakersfield, Calif.

Young shoot:
- *Openness of tip.*—Slightly open.
- *Prostrate hairs on tip.*—Sparse.
- *Anthocyanin coloration of prostate hairs on tip.*—Weak.
- *Erect hairs on tip.*—Sparse.

Young leaf:
- *Color of upper side of blade.*—Yellow-green 146-C.
- *Prostrate hairs between main veins on lower side of blade.*—Sparse.
- *Erect hairs on main veins on lower side of blade.*—Sparse.

Shoot:
- *Attitude (before tying).*—Semi-erect.
- *Color of dorsal side of internodes.*—Green (yellow green 143-C).
- *Color of ventral side of internodes.*—Green (yellow green 143-C).
- *Color of dorsal side of nodes.*—Green (yellow green 143-C).
- *Color of ventral side of nodes.*—Green (yellow green 143-C).
- *Erect hairs on internode.*—Absent or very sparse.
- *Length of tendrils.*—Long (7.5").
- *Color of tendrils.*—Yellow green (144-B).
- *Number of tendrils.*—5.

Flower:
- *Sexual organs.*—Fully developed stamens and fully developed gynoecium.

Mature leaf:
- *Size of blade.*—Very large (7"×6.5").
- *Shape of blade.*—Wedge-shaped.
- *Blistering of upper side of blade.*—Weak.
- *Number of lobes.*—Five.
- *Depth of upper lateral sinuses.*—Deep.
- *Arrangement of lobes of upper lateral sinuses (only varieties with lobed leaves).*—Slightly overlapped.
- *Arrangement of lobes petiole sinus.*—Half open.
- *Length of teeth.*—Medium.
- *Ratio length/width of teeth.*—Medium.
- *Shape of teeth.*—Both sides straight.
- *Proportion of main veins on upper side of blade with anthocyanin coloration.*—Medium.
- *Prostrate hairs between main veins on lower side of blade.*—Sparse.
- *Erect hairs on main veins on lower side of blade.*—Sparse.
- *Length of petiole compared to length of middle vein.*—Equal.
- *Top side color.*—Green (137-B).
- *Bottom side color.*—Yellow Green (137-D).
- *Texture.*—Smooth.
- *Vein color.*—Yellow Green (143-C).
- *Petiole length.*—7".
- *Petiole color.*—Yellow Green (143-C).

Reproductive organs:
- *Color.*—Green (138-A).
- *Size.*—0.002900".

Time of beginning of ripening: Jan. 10, 2013 in Bakersfield, Calif.

Bunch:
- *Size (penduncle excluded).*—Large.
- *Density.*—Lax.
- *Length of penduncle primary bunch.*—Medium.
- *Average bunch weight.*—1.5 lbs.

Berry:
- *Size.*—Medium.
- *Length.*—1".
- *Shape.*—Obtuse ovoid.
- *Diameter.*—14/16".
- *Weight.*—8-10 grams.
- *Color of skin (without bloom).*—Red.
- *Ease of detachment from pedicle.*—Difficult.
- *Thickness of skin.*—Medium.
- *Anthocyanin coloration of flesh.*—Weak.
- *Firmness of flesh.*—Moderately firm.
- *Particular flavor.*—None.

*Formation of seeds.*—None.

*Market use of observed plant.*—Fresh market.

*Berries per bunch.*—100-120 berries.

Woody shoot:

*Main color.*—Dark brown (grayed orange 166-C AND 176-B).

Age and growing conditions: Six years growing under Y system in South Joaquin Valley (hot, dry summers).

Shipping characteristics: (E.g. number of days fruit has been stored under specific conditions):

*Fruit was in cold storage.*—Stored in poly bags inside Styrofoam boxes with sulphur pads.

*After* 60 *days.*—Rachises were 75% green; 2% berry shuttering; no berry wrinkling or cracks were apparent.

DNA PROFILE

To further the characterize the new Arra variety DNA was extracted from dried leaf samples and DNA profiles were obtained at California Seed & Plant Lab, California USA using base pairs for 10-standard microsatellite DNA markers. The data is presented hereafter.

| Microsatellite DNA Marker | Allele Sizes in Base Pairs | |
|---|---|---|
| M 1 | 234 | 236 |
| M 2 | 239 | 243 |
| M 3 | 179 | 181 |
| M 4 | 212 | 214 |
| M 5 | 251 | 251 |
| M 6 | 135 | 151 |
| M 7 | 187 | 187 |
| M 8 | 255 | 259 |
| M 9 | 211 | 214 |
| M 10 | 247 | 261 |

The 'ARRATWENTYEIGHT' variety has not been observed under all possible environmental conditions to date. Accordingly, it is possible that the phenotypic expression may vary somewhat with changes in light intensity and duration, cultural practices, and other environmental conditions.

What is claimed is:

1. A new and distinct variety of grapevine, botanically known as *Vitis vinifera*, identified as 'ARRATWENTYEIGHT', substantially as shown and described herein.

* * * * *

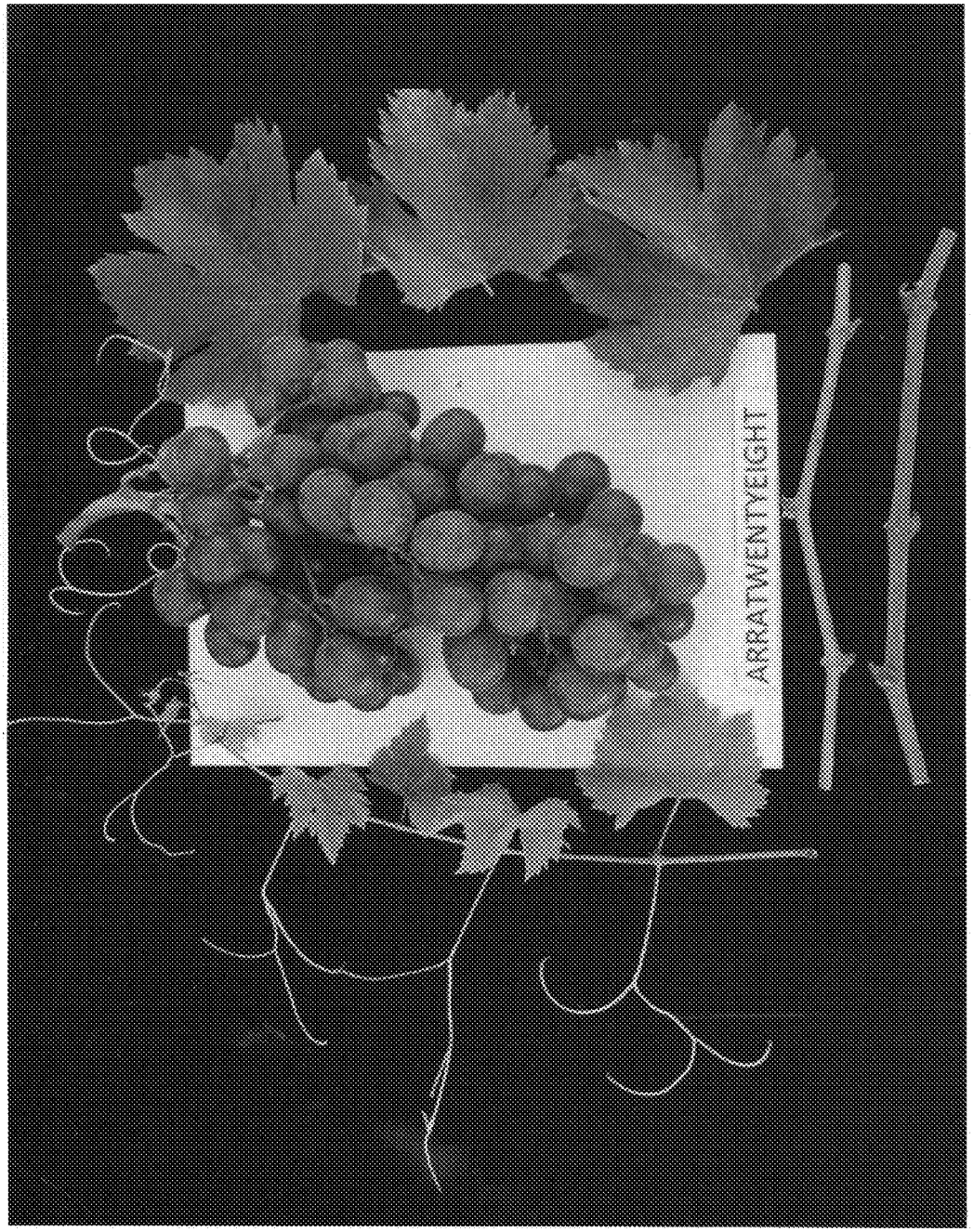
ARRATWENTYEIGHT